United States Patent [19]

Acquati et al.

[11] 4,291,121

[45] Sep. 22, 1981

[54] BILIRUBIN-RESISTANT DETERMINATION OF URIC ACID AND CHOLESTEROL

[75] Inventors: Giancarlo Acquati, Robbiate; Giovanni Berti, Malgrate; Piero Fossati, Lissone, all of Italy

[73] Assignee: Miles Laboratories, Inc., Elkhart, Ind.

[21] Appl. No.: 133,533

[22] Filed: Mar. 24, 1980

Related U.S. Application Data

[63] Continuation-in-part of Ser. No. 29,670, Apr. 13, 1979, abandoned.

[51] Int. Cl.³ .................. G01N 33/52; G01N 33/92; G01N 33/72
[52] U.S. Cl. .................. 435/10; 23/230 B; 23/909; 23/925; 252/408; 422/56; 435/11; 435/28; 435/805
[58] Field of Search ............ 23/230 B, 925, 40; 422/56; 252/408; 435/28; 435/10, 11

[56] References Cited

U.S. PATENT DOCUMENTS

| Re. 29,498 | 12/1977 | Meiattini | 435/28 X |
|---|---|---|---|
| 4,095,948 | 6/1978 | Hunziker | 252/408 X |
| 4,184,921 | 1/1980 | Roeschlav | 435/11 |
| 4,186,251 | 1/1980 | Tarbutton | 435/11 |
| 4,247,631 | 1/1981 | Nix | 435/10 |
| 4,251,629 | 2/1981 | Yamanisi | 435/10 X |

OTHER PUBLICATIONS

"Hackh's Chemical Dictionary," J. Grant, ed., 4th Edition, p. 507, McGraw-Hill, New York, 1969.

Primary Examiner—Sidney Marantz
Attorney, Agent, or Firm—Charles J. Herron

[57] ABSTRACT

A composition, test device, method of making a test device and process for bilirubin-resistant determination of an analyte selected from uric acid or cholesterol in a fluid sample are disclosed. More particularly, the composition is of the type comprising means responsive to the presence of the particular analyte to be determined in the sample, a phenol and 4-aminophenazone to which resistance to interference by bilirubin is imparted by inclusion therein of reagent means comprising a ferrocyanide ion. The uric acid or cholesterol responsive means is preferably of the type which determines peroxides formed from enzymatic conversion of the analyte. The composition can optionally be incorporated with a carrier to provide a test device.

17 Claims, No Drawings

BILIRUBIN-RESISTANT DETERMINATION OF URIC ACID AND CHOLESTEROL

CROSS-REFERENCE TO RELATED APPLICATION

This application is a continuation-in-part of U.S. Ser. No. 29,670, filed Apr. 13, 1979, abandoned.

FIELD OF THE INVENTION

The present invention relates generally to the field of diagnostic tests and, more particularly, to those tests useful in qualitative and quantitative determination of analytes selected from uric acid or cholesterol in body fluids such as urine or blood. More particularly, it relates to those tests in which the analyte is converted to an oxidizing substance, such as a peroxide.

BACKGROUND OF THE INVENTION

The oxidative coupling reaction between phenol and 4-aminophenazone, also known as 4-aminoantipyrine, to give a red quinoneimine dye has been known for a long time, having been described by Emerson, J. Org. Chem. 8:417 (1943).

The reaction has gained popularity in clinical chemistry since the application made by Trinder, [Ann. Clin. Biochem, 6:24 (1969)] to the enzymatic determination of glucose, based on the reaction scheme:

glucose + $O_2$ $\xrightarrow{\text{glucose oxidase}}$ gluconic acid + $H_2O_2$ $2H_2O_2$ + phenol + 4-aminophenazone $\xrightarrow{\text{peroxidase}}$ quinoneimine dye + $4H_2O$ The chromogenic system phenol (including substituted phenols) +4-aminophenazone+peroxidase, referred to as the Emerson-Trinder system, is now used in the quantitative determination not only of glucose, but also of cholesterol and uric acid in serum, plasma or other biological fluids. Use of this system for the determination of glucose is disclosed in Meiattini, U.S. Pat. No. 3,886,045, now reissued as U.S. Pat. No. Re 29,498.

The general scheme of the reaction is the following:

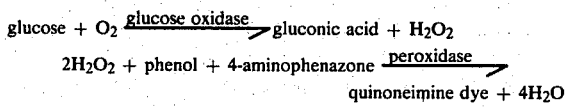

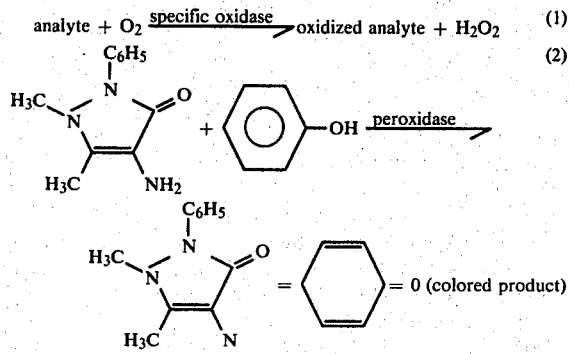

Many phenols can be used in the Emerson-Trinder reaction. Examples of those most commonly used in clinical chemistry are phenol; p-hydroxybenzoate; 2,4-dichlorophenol; 3,5-dichloro-2-hydroxybenzenesulfonic acid. Likewise various substituted and unsubstituted napthols can be used.

The sample constituents which can be determined include glucose, cholesterol, uric acid or other metabolites which can be oxidized by a specific oxidase with contemporaneous formation of hydrogen peroxide. The oxidase is glucose oxidase for determining glucose; cholesterol oxidase for determining cholesterol (cholesterol ester hydrolase is also added to hydrolyze esterified cholesterol); and uricase for uric acid determinations.

The amount of dye formed is proportional to the concentration of the hydrogen peroxide and, therefore, to the concentration of the constituent in the sample. Thus, the concentration of the constituent in the sample can be obtained by a simple measurement of the absorbance of the reacted solution and comparison of such measurement to that of a known standard solution of the constituent.

The dye formed can be measured in the visible range, generally between 500 and 550 nanometers (nm) (depending on the phenol used); requiring only a colorimeter or a visible color range photometer.

The Emerson-Trinder chromogenic system suffers the major disadvantage that the oxidative coupling reaction is affected by reducing compounds and bilirubin, a metabolite which is usually present in serum in concentrations not higher than 1 milligram per deciliter (mg/dl), but which can reach very high levels (20 or more mg/dl) in some diseases. Levels of bilirubin higher than normal affect the enzymatic glucose, cholesterol and uric acid tests by decreasing the color of the reaction. Interference increases with the increase of the bilirubin level.

The explanation of negative interference of reducing compounds (e.g. ascorbic acid) is quite obvious, since they act chiefly as competitors with the chromogen in the peroxidase catalyzed reaction with hydrogen peroxide, or as bleaching agents on the color formed. The interference of reducing substances, however, is not a real problem, at least in serum, where ascorbic acid rarely exceeds 3 mg/dl.

In contrast, the interference by bilirubin is a significant problem for the determination of metabolites in serum through the Emerson-Trinder chromogenic system, and represents a major negative aspect of this system in routine laboratory practice, where hyperbilirubinemic samples are frequently found.

The mechanism of reaction of bilirubin is quite complex and, as yet, not fully understood. The best approach so far afforded to the problem is that of Witte [Clin. Chem. 24:1778 (1978)], who ascribes the interference of bilirubin to one or more of the following factors: simple spectral effects, acting as an alternative peroxidase substrate, or destruction of peroxidase reaction intermediates.

OBJECTS OF THE INVENTION

It is therefore an object of the present invention to provide an improved test for the detection of an analyte selected from uric acid or cholesterol in a fluid sample.

A further object of the invention is to provide an improved test for the detection of an analyte selected from uric acid or cholesterol which is highly resistant to the interfering effects of bilirubin.

Other objects and a fuller understanding of the invention will be had by referring to the following description and claims drawn to preferred embodiments thereof.

SUMMARY OF THE INVENTION

As part of the present invention it has been discovered that bilirubin strongly interferes with chromogenic tests of the type having a substituted or unsubstituted phenol and 4-aminophenazone, chiefly by two different mechanisms: (1) by overlapping the spectrum of the dye formed in the reaction, thereby causing a positive interference, and (2) by a chemical mechanism, as previously discussed, which causes a negative interference. The positive interference resulting from the first mechanism, can be reduced by reading the absorbance at a wavelength of 520 nm or higher. However, such is not the case with respect to the second mechanism. It plays an extremely important role, causing inaccurate results in the above-described tests when bilirubin is present in the sample in abnormal concentrations.

In contrast to prior art compositions, that of the present invention is highly sensitive to the presence of an analyte selected from uric acid or cholesterol in body fluids, while also being substantially resistant to bilirubin interference.

This surprising result is achieved, in accordance with the present invention, by a composition for the detection of an analyte selected from uric acid or cholesterol in a fluid sample of the type comprising means responsive to the presence of said analyte in the sample, phenol and 4-aminophenazone and to which resistance to interference by bilirubin is imparted by inclusion therein of reagent means comprising a ferrocyanide ion.

DESCRIPTION OF THE PREFERRED EMBODIMENTS

Although specific terms are used in the following description for the sake of clarity, these terms are intended to refer only to the particular embodiment of the invention selected for exemplary illustration, and are not intended to define or limit the scope of the invention.

The composition according to the invention can take many physical forms and include a phenol, including substituted and unsubstituted phenols, well known for its applicability of use with 4-aminophenazone indicator compositions, in combination with the reagent means which comprises a ferrocyanide ion. These, along with materials such as stabilizing agents and other conventional additives, which can additionally be employed if desired, are described.

Preferred reagent means comprising a ferrocyanide ion include alkali metal salts of ferrocyanide, such as sodium or potassium ferrocyanide, as well as any other source of ferrocyanide ion, including any other salt or system containing or capable of releasing $Fe(CN)_6^{-4}$ ions.

The composition comprises along with the reagent means according to the invention, means responsive to the presence of an analyte selected from uric acid or cholesterol in a fluid sample to produce an oxidizing substance. Such analyte responsive means are preferably enzymatic in nature and preferably comprise a peroxidatively active substance, uricase for the determination of uric acid and cholesterol oxidase for the determination of cholesterol. The concentrations and types of reagents useful in the analyte responsive means are contemplated to include those known to the art.

The test means can be used as a solution for determination of the analyte. The solvents used in preparing the solutions can be water, physiological solutions, organic solvents, such as methanol, or mixtures thereof.

The composition is preferably used to detect the analyte by adding it to a specimen such as urine, cerebrospinal fluid, tissue culture supernatant and preferably, serum, plasma or whole blood.

When the composition is used in solution form the reagent means comprising the ferrocyanide ion is preferably used in concentrations of from about 1.0 micromol/liter ($\mu$mol/l) to a saturated solution. The preferred range is from about 5 $\mu$mol/l to about 50 $\mu$mol/l. When uricase is part of the analyte responsive means, concentrations thereof are perferably from about 10 International Units (I.U.)/liter (l) to about 200 I.U./l. When cholesterol oxidase is part of the analyte responsive means, concentrations thereof are preferably from about 10 I.U./l to about 200 I.U./l. When cholesterol ester hydrolase is used to obtain determinations of total cholesterol concentrations thereof are preferably from about 10 I.U./l to about 200 I.U./l. When peroxidase is at least one of the reagents comprising the analyte responsive means concentrations of the peroxidase are preferably from about 10 I.U./l to about 200 I.U./l.

The enzyme activity is expressed in International Units (I.U.), one I.U. being the amount of enzyme activity required to catalyze the conversion of 1 micromol ($\mu$mol) of substrate per minute under specified conditions of pH and temperature. Horseradish peroxidase, uricase and cholesterol oxidase used in the examples can be obtained from Research Products Division, Miles Laboratories, Inc., Elkhart, Ind.

Also provided are test devices incorporating the composition of the invention and a method of making such test devices which comprises incorporating a carrier, such as a matrix, with the composition. When this incorporation is by inpregnation with a solution of the composition according to the invention the carrier so impregnated is then dried. In addition to impregnation, the devices of the present invention can be made by other suitable incorporating techniques, such as printing or spraying the composition onto a substrate or matrix. Alternatively, the compositions of the invention can be embodied in a carrier taking the form of a pressed or molded tablet containing conventional carrier material.

The term carrier refers to matrices which are insoluble in and maintain there structural integrity when exposed to physiological or other liquid. Suitable matrices which may be used include paper, cellulose, wood, synthetic resin fleeces, glass fiber, nonwoven and woven fabrics, gelatin, various organic polymers, such as polypropylene, and other organic materials well known as film formers to those skilled in the art. For convenience, the carrier or test device can be associated with an insoluble support or handle member, such as can be made with polystyrene.

When the test composition is to be used for detecting uric acid or cholesterol in blood, the surface of the impregnated carrier matrix is advantageously covered with a semipermeable transparent coating film of ethyl cellulose or other suitable material. This can be accomplished by applying a layer of ethyl cellulose dissolved in benzene, for example, to the surface of the impregnated carrier matrix and then removing the solvent by evaporative drying.

Indicators in the form of treated carrier matrices or test devices are often stored for considerable periods of time before use, and it is therefore desirable that the reagents chosen are not easily autoxidizable in air. Advisably, the test devices should be protected from exposure to light, and in some cases it is desirable to keep them sealed in a moisture repellent package which is opened only for the purpose of removing one or more test devices shortly before use thereof.

If desirable, a carrier matrix can be treated with a background dye of a particular color, such as yellow, so that the color produced by the test reaction blends with the background color to produce varying tints corresponding to the concentration of the sample constituent.

The device is preferably prepared by a single dip process. The concentrations of reagents used in the dip range from about $10^{-3}$ mM up to a saturated solution. Most generally useful for the 4-aminophenazone is a concentration of about 0.2 mM. Peroxidase concentration is from about 0.1 mg/dl about 20 mg/dl in the dip solution. The solvents used in preparing the impregnating solution can be water, physiological solutions, organic solvents or combinations thereof.

The test device is advantageously used by momentarily dipping it in a test sample or by otherwise introducing a test sample onto the carrier matrix, whereby a detectable color change results thereon when the analyte is present. The test device can be used in the same way whether samples of plasma, serum or other body fluids are tested. However, when testing whole blood it is preferred that a drop of blood be contacted with the surface of the device.

The examples shown are merely illustrative and are not to be construed as a limitation of the invention. One skilled in the art will be able to make such variations, substitutions and changes in the ingredients and parameters as may seem desirable.

EXAMPLE 1

Determination of uric acid in serum with uricase and peroxidase/3,5-dichloro-2-hydroxybenzenesulfonic acid/4-aminophenazone Test solutions were prepared according to the prior art and the present invention and compared as to their resistance to the interfering effects of bilirubin in the determination of uric acid.

Test solutions were prepared in accordance with the prior art having the following formulation:

| | |
|---|---|
| phosphate buffer | 150 mmol/l, pH 7.0 |
| uricase | 60 I.U./l |
| peroxidase | 140 I.U./l |
| 4-aminophenazone | 0.24 mmol/l |
| 3,5-dicholoro-2-hydroxy-benzenesulfonic acid | 2.0 mmol/l |

Test solutions incorporating the composition of the invention were prepared exactly as above but with the addition of 20 μmol/l potassium ferrocyanide [$K_4Fe(CN)_6$].

A 2.0 ml aliquot of prior art test solution was pipetted into each of a first group of test tubes and a 2.0 ml aliquot of the solution of the composition of the invention was pipetted into each of a second group of test tubes. A parallel series of samples was introduced to the test tubes of each group.

Serum samples were obtained, pooled and tested for contents of uric acid and bilirubin. Uric acid was added to the pooled sera to a concentration of 6.0 mg/dl and the solution was separated into aliquots. Amounts of bilirubin were added so as to provide uric acid test solution samples respectively having bilirubin concentrations of 0.7, 1.4, 2.2, 3.6, 5.0, 6.5, 8.8, 12.1, 16.7 and 23.4 mg/dl. Other uric acid solution aliquots, having no bilirubin, were used as a standard solution.

Each group of test tubes was injected with a parallel series of 0.05 ml sample aliquots containing the various bilirubin concentrations and the reaction in these tests tubes was allowed to go forward for 15 minutes at room temperature. The absorbance readings were performed at 520 nm against the corresponding sample blanks obtained by omitting uricase from the reagent formulations.

The results reporting the percent recovery of uric acid in tests using the prior art and the inventive test compositions at the various bilirubin concentrations are shown in Table 1.

TABLE 1

| | Uric acid Observed (percent recovery) | |
|---|---|---|
| Bilirubin (mg/dl) | With $K_4 Fe(CN)_6$ | Without $K_4 Fe(CN)_6$ |
| 0.7 | 100.0 ± 1.2 | 100.0 ± 1.2 |
| 1.4 | 100.0 | 97.2 |
| 2.2 | 99.2 | 93.5 |
| 3.6 | 98.0 | 83.6 |
| 5.0 | 97.0 | 78.5 |
| 6.5 | 95.9 | 71.5 |
| 8.8 | 93.4 | 59.0 |
| 12.1 | 91.0 | 43.5 |
| 16.7 | 90.0 | 21.0 |
| 23.4 | 89.0 | |

A remarkable chemical interference (about 6%) is noticed in the uric acid test in the absence of ferrocyanide even at levels of bilirubin as low as 2 mg/dl, and this is even more dramatic (more than 20%) at the 5 mg/dl level.

When ferrocyanide is used, the chemical interference from bilirubin is strongly reduced (statistically not significant at 2 mg/dl bilirubin; 3% at 5 mg/dl; around 10% at levels of bilirubin as high as 15–20 mg/dl).

EXAMPLE II

Test device for determination of uric acid in urine with uricase and peroxidase/3,5-dichloro-2-hydroxybenzenesulfonic acid/4-aminophenazone Test devices incorporating compositions according to the prior art and the present invention were prepared and compared as to their resistance to the interfering effects of bilirubin in testing for the presence of uric acid in urine.

An impregnation solution according to the prior art was prepared to have the following formulation:

| | |
|---|---|
| phosphate buffer | 150 mmol, pH 7.0 |
| uricase | 150 I.U. |
| peroxidase | 860 I.U. |
| 4-aminophenazone | 0.24 mmol |
| 3,5-dichloro-2-hydroxy-benzenesulfonic acid | 2 mmol |
| $H_2O$ | to 1000 ml |

Impregnation solutions incorporating a composition of the present invention were prepared exactly as above but with the addition of 20 μmol/of potassium ferrocyanide [$K_4Fe(CN)_6$].

Sheets of Whatman No. 17 filter paper (Whatman, Inc. Clifton, N.J.) were impregnated to saturation with the impregnation solutions and dried at 60° Centigrade (C.). These sheets containing the dried residue of the impregnating solutions were cut to 2.5 millimeters (mm)×2.5 mm to form devices. The devices were then backed with double-faced adhesive tape and fixed thereby to plastic handles.

Urine samples were obtained, pooled and tested for contents of uric acid and bilirubin. The pooled urine was then diluted with 10 volumes of distilled water. Uric acid was added to the diluted urine pool until a concentration of 6 mg/dl of uric acid was achieved. Then, bilirubin was added to the diluted urine pool up to a concentration of 10 mg/dl, thus providing a test solution. This test solution was divided into aliquots.

Test devices according to the invention were momentarily immersed in one aliquot of the uric acid test solution and test devices according to the prior art were momentarily immersed in another aliquot thereof. The test devices were visually examined for color change after about 10 minutes.

Devices prepared in accordance with the invention showed a distinct change in color indicating the presence of uric acid whereas the test devices containing the prior art composition did not change color, thereby reporting a false negative for uric acid.

EXAMPLE III

Determination of cholesterol with cholesterol oxidase/cholesterol ester hydrolase and peroxidase/phenyol/4-aminophenazone Test solutions were prepared according to the prior art and the present invention and compared as to their resistance to the interfering effects of bilirubin in the determination of cholesterol.

Test solutions were prepared in accordance with the prior art having the following formulaton:

| | |
|---|---|
| phosphate buffer | 100 mmol/l, pH 7.7 |
| cholesterol ester hydrolase | 80 I.U./l |
| cholesterol oxidase | 40 I.U./l |
| peroxidase | 500 I.U./l |
| 4-aminophenazone | 0.5 mmol/l |
| phenol | 10 mmol/l |
| sodium cholate | 3 mmol/l |
| Triton X-100 | 0.5% volume/volume (v/v) |

Test solutions incorporating the composition of the invention were prepared exactly as above but with the addition of 12 mmol/l potassium ferrocyanide $[K_4Fe(CN)_6]$.

A 2.5 ml aliquot of the prior art test solution was pipetted into each of a first group of test tubes and a 2.5 ml aliquot of the solution of the composition of the invention was pipetted into each of a second group of test tubes. A parallel series of samples was introduced to the test tubes of each group.

An aqueous cholesterol solution was prepared to have a concentration 200 mg/dl and the solution was separated into aliquots. Amounts of bilirubin were added so as to provide cholesterol solution samples respectively having bilirubin concentrations of 1.3, 3.8, 6.3, 9.8, 12.0, 13.5, and 18.3 mg/dl. Other cholesterol solution and the working solution was used to calibrate a blank value.

Each group of test tubes was injected with a parallel series of 0.02 ml sample aliquots containing the various bilirubin concentrations and the reaction in these test tubes was allowed to go forward for 15 minutes at 37° C. The absorbance readings were performed and the cholesterol concentrations calculated using the same method and formula as was used for uric acid in Example I.

The results reporting the amount of cholesterol observed in tests using the prior art and the inventive test systems at the various bilirubin concentrations are shown in Table 2.

TABLE 2

| | Cholesterol Observed (percent recovery) | |
|---|---|---|
| Bilirubin (mg/dl) | With $K_4Fe(CN)_6$ | Without $K_4Fe(CN)_6$ |
| 1.3 | 100.0 ± 1.7 | 100.0 ± 1.7 |
| 3.8 | 99.2 | 97.1 |
| 6.3 | 98.3 | 93.0 |
| 9.8 | 97.8 | 87.1 |
| 12.0 | 97.9 | 85.4 |
| 13.5 | 97.6 | 85.8 |
| 18.3 | 97.9 | 80.5 |

The chemical intereference in the cholesterol test in the absence of ferrocyanide is remarkable. However, in the presence of ferrocyanide the interference is so stongly reduced that it can, for practical purposes, be considered as negligible up to at least 18 mg bilirubin/dl.

EXAMPLE IV

Test device for determination of cholesterol in serum with cholesterol oxidase and peroxidase/3,5-dichloro-2-hydroxy-benzenesulfonic acid/4-aminophenazone Test devices incorporating compositions according to the prior art and the present invention were prepared and compared as to their resistance to the interfering effects of bilirubin in testing for the presence of cholesterol in serum.

An impregnation solution according to the prior art was prepared to have the following formulation:

| | |
|---|---|
| phosphate buffer | 100 mmol/l, pH 7.7 |
| cholesterol ester hydrolase | 240 I.U./l |
| cholesterol oxidase | 120 I.U./l |
| peroxidase | 2,500 I.U./l |
| 4-aminophenazone | 0.5 mmol/l |
| 3,5-dichloro-2-hydroxybenzene sulfonic acid | 10 mmol/l |
| sodium cholate | 3 mmol/l |
| Triton X-100 | 0.5% volume/volume (v/v) |

Impregnation solutions incorporating a composition of the present invention were prepared exactly as above but with the addition of 20 µmol/l of potassium ferrocyanide $[K_4FE(CN)_6]$.

Sheets of Whatman No. 17 filter paper (Whatman, Inc. Clifton, N.J.) were impregnated to saturation with the impregnation solutions and dried at 60° Centigrade (C.). These sheets containing the dried residue of the impregnating solutions were cut to 2.5 millimeters (mm)×2.5 mm to form devices. The devices were then backed with double-faced adhesive tape and fixed thereby to plastic handles.

Serum samples were obtained, pooled and tested for contents of cholesterol (which was around 200 mg/dl) and bilirubin. The pooled serum was then diluted with 10 volumes of distilled water. The bilirubin was added to the diluted serum pool up to a concentration of 20 mg/dl, thus providing a test solution. This test solution was divided into aliquots.

Test devices according to the invention were momentarily immersed in one aliquot of the cholesterol test solution and test devices according to the prior art were momentarily immersed in another aliquot thereof. The test devices were visually examined for color change after about 10 minutes.

Devices prepared in accordance with the invention showed a distinct change in color indicating the presence of cholesterol whereas the test devices containing the prior art composition did not change color, thereby reporting a false negative for cholesterol.

Although the invention has been described with a certain degree of particularity, it is understood that the present disclosure has been made only by way of example and that numerous changes in the details may be resorted to without departing from the scope of the invention.

What is claimed is:

1. Composition for the determination of an analyte selected from uric acid and cholesterol in a fluid sample of the type comprising means responsive to the presence of said analyte in said sample, a phenol or napthol and 4-aminophenazone wherein the improvement comprises reagent means comprising a ferrocyanide ion.

2. The composition of claim 1 wherein the phenol is an unsubstituted phenol.

3. The composition of claim 1 wherein the phenol is 3,5-dichloro-2-hydroxybenzenesulfonic acid.

4. The composition of claim 1 wherein the reagent means is a ferrocyanide ion salt.

5. The composition of claim 4 wherein the ferrocyanide ion salt is sodium ferrocyanide.

6. The composition of claim 4 wherein the ferrocyanide ion salt is potassium ferrocyanide.

7. The composition of claim 1 wherein the analyte is uric acid.

8. A composition for the determination of uric acid in a fluid sample of the type comprising means responsive to the presence of uric acid on the sample, unsubstituted phenol and 4-aminophenazone wherein the improvement comprises reagent means comprising potassium ferrocyanide.

9. The composition of claim 1 wherein the analyte is cholesterol.

10. A composition for the determination of cholesterol in a fluid sample of the type comprising means responsive to the presence of cholesterol in the sample, unsubstituted phenol and 4-aminophenazone wherein the improvement comprises reagent means comprising sodium ferrocyanide.

11. A test device which comprises a carrier incorporated with the composition of claim 1.

12. A method of making a test device which comprises incorporating a carrier with the composition of claim 1.

13. The method of claim 12 wherein the composition is incorporated with the carrier by impregnating the carrier with a solution of said test means, followed by drying of the impregnated carrier.

14. A process for determination of uric acid in a fluid sample which comprises contacting said sample with the composition of claim 1 and observing any resultant color formed.

15. A process for determination of uric acid in a fluid sample which comprises contacting said sample with the test device of claim 11 and observing any resultant color formed thereon.

16. A process for determination of cholesterol in a fluid sample which comprises contacting said sample with the composition of claim 1 and observing any resultant color formed.

17. A process for determination of cholesterol in a fluid sample which comprises contacting said sample with the test device of claim 11 and observing any resultant color formed thereon.

* * * * *